US009492542B2

(12) United States Patent
Guglielmotti et al.

(10) Patent No.: US 9,492,542 B2
(45) Date of Patent: Nov. 15, 2016

(54) PHARMACEUTICAL COMPOSITION FOR THE TREATMENT OF MCP-1 MEDIATED INFLAMMATORY DISEASES

(75) Inventors: Angelo Guglielmotti, Rome (IT); Beatrice Garrone, Rome (IT); Alessandro Ble', Aprilia (IT); Giuseppe Biondi, Castel Gandolfo (IT); Roberta Petrosemolo, legal representative, Castel Gandolfo (IT); Enrica Biondi, legal representative, Nerviano (IT); Iacopo Biondi, legal representative, Castellanza (IT)

(73) Assignee: AZIENDE CHIMICHE RIUNITE ANGELINI FRANCESCO A.C.R.A.F. S.p.A., Rome (IT)

( * ) Notice: Subject to any disclaimer, the term of this patent is extended or adjusted under 35 U.S.C. 154(b) by 572 days.

(21) Appl. No.: 13/497,175
(22) PCT Filed: Sep. 3, 2010
(86) PCT No.: PCT/EP2010/062979
§ 371 (c)(1),
(2), (4) Date: May 2, 2012
(87) PCT Pub. No.: WO2011/036047
PCT Pub. Date: Mar. 31, 2011

(65) Prior Publication Data
US 2012/0220636 A1 Aug. 30, 2012

(30) Foreign Application Priority Data
Sep. 23, 2009 (EP) .................................... 09425368

(51) Int. Cl.
A61K 31/425 (2006.01)
A61K 45/06 (2006.01)
(Continued)

(52) U.S. Cl.
CPC ............. *A61K 45/06* (2013.01); *A61K 31/165* (2013.01); *A61K 31/366* (2013.01); *A61K 31/40* (2013.01);
(Continued)

(58) Field of Classification Search
CPC . A61K 31/415; A61K 31/416; A61K 31/478
USPC .................................................. 514/367, 369
See application file for complete search history.

(56) References Cited

U.S. PATENT DOCUMENTS 4,999,367 A 3/1991 Baiocchi et al.
5,112,986 A 5/1992 Baiocchi et al.
(Continued)

FOREIGN PATENT DOCUMENTS

EP 0 173 481 A2 3/1986
EP 0 266 950 A2 5/1988
(Continued)

OTHER PUBLICATIONS

Candido et al., Circulation, 2004;109:1536-1542.*
U.S. Appl. No. 13/898,950, filed May 21, 2013, Guglielmotti, et al.
International Search Report issued Nov. 15, 2010, in PCT/EP2010/062979.
(Continued)

*Primary Examiner* — San-Ming Hui
(74) *Attorney, Agent, or Firm* — Oblon, McClelland, Maier & Neustadt, L.L.P.

(57) ABSTRACT

The present invention relates to a pharmaceutical composition comprising a combination of 1-benzyl-3-hydroxymethylindazole derivative, a pressure lowering agent selected from ACE-inhibitors, renin inhibitors, ARBs and CCBs, and/or a cholesterol lowering agent selected from statin derivatives. The combination showed an additive and synergistic activity in reducing MCP-1 levels, thus significantly improving inflammatory response inhibition and consequently reducing complications occurring in patients suffering from inflammatory diseases.

10 Claims, 2 Drawing Sheets

(51) Int. Cl.

| | | |
|---|---|---|
| *A61K 31/165* | (2006.01) | |
| *A61K 31/366* | (2006.01) | |
| *A61K 31/40* | (2006.01) | |
| *A61K 31/403* | (2006.01) | |
| *A61K 31/415* | (2006.01) | |
| *A61K 31/416* | (2006.01) | |
| *A61K 31/4178* | (2006.01) | |

(52) U.S. Cl.
CPC ........... *A61K 31/403* (2013.01); *A61K 31/415* (2013.01); *A61K 31/416* (2013.01); *A61K 31/4178* (2013.01)

(56) References Cited

U.S. PATENT DOCUMENTS

| | | | |
|---|---|---|---|
| 5,209,933 | A | 5/1993 | MacFarlane et al. |
| 5,278,183 | A | 1/1994 | Silvestrini |
| 5,393,875 | A | 2/1995 | Branca et al. |
| 5,559,111 | A | 9/1996 | Göschke et al. |
| 5,688,946 | A | 11/1997 | Branca et al. |
| 5,977,159 | A | 11/1999 | Fändriks et al. |
| 6,020,356 | A | 2/2000 | Guglielmotti et al. |
| 6,268,377 | B1 | 7/2001 | Waldstreicher et al. |
| 6,342,247 | B1* | 1/2002 | Ku et al. ............... 424/465 |
| 6,534,534 | B1* | 3/2003 | Guglielmotti et al. ....... 514/403 |
| 6,911,472 | B2 | 6/2005 | Hegde et al. |
| 7,183,285 | B2 | 2/2007 | Griffin et al. |
| 7,459,447 | B2 | 12/2008 | Aoki et al. |
| 7,498,359 | B2 | 3/2009 | Yokoyama et al. |
| 7,919,518 | B2 | 4/2011 | Guglielmotti et al. |
| 2003/0060500 | A1 | 3/2003 | Mach |
| 2003/0060501 | A1 | 3/2003 | Mach |
| 2003/0060502 | A1 | 3/2003 | Mach |
| 2003/0065019 | A1 | 4/2003 | Mach |
| 2008/0139511 | A1 | 6/2008 | Friesen |
| 2009/0156636 | A1 | 6/2009 | Nakagawa |
| 2010/0317618 | A1 | 12/2010 | Guglielmotti et al. |
| 2011/0003874 | A1 | 1/2011 | Guglielmotti et al. |
| 2011/0082141 | A1 | 4/2011 | Guglielmotti et al. |
| 2011/0160205 | A1 | 6/2011 | Guglielmotti et al. |

FOREIGN PATENT DOCUMENTS

| | | |
|---|---|---|
| EP | 0 311 012 A2 | 4/1989 |
| EP | 0 382 276 A2 | 8/1990 |
| EP | 0 382 276 A3 | 8/1990 |
| EP | 0 416 373 A2 | 3/1991 |
| EP | 0 456 185 A2 | 11/1991 |
| EP | 0 509 354 A2 | 10/1992 |
| EP | 0 510 748 A1 | 10/1992 |
| EP | 0 382 276 B1 | 8/1995 |
| EP | 0 510 748 B1 | 3/1996 |
| EP | 1 005 332 B1 | 10/2003 |
| EP | 1 806 137 A1 | 7/2007 |
| WO | WO 97/16185 A2 | 5/1997 |
| WO | WO 97/16185 A3 | 5/1997 |
| WO | WO 99/04770 A2 | 2/1999 |
| WO | WO 02/092081 A1 | 11/2002 |
| WO | WO 2008/084504 A2 | 7/2008 |
| WO | WO 2008/104580 A1 | 9/2008 |
| WO | WO 2009/109613 A2 | 9/2009 |
| WO | WO 2009/109613 A3 | 9/2009 |

OTHER PUBLICATIONS

Barrett J. Rollins, "Chemokines", Blood, vol. 90, (1997), pp. 909-928.
Marco Baggiolini, "Chemokines and leukocyte traffic", Nature, vol. 392, Apr. 9, 1998, pp. 565-568.
Craig Gerard, et al., "Chemokines and disease", Chemokine Reviews, Nature Immunology, vol. 2, No. 2, Feb. 2001, pp. 108-115.
Surendran Mahalingam, et al., "Chemokines and viruses: friends or foes?", Trends in Microbiology, vol. 11, No. 8, Aug. 2003, pp. 383-391.
Nestor E. Rulli, et al., "Ross River virus: molecular and cellular aspects of disease pathogenesis", Pharmacology & Therapeutics, vol. 107, (2005), pp. 329-342.
M. Sironi, et al., "A small synthetic molecule capable of preferentially inhibiting the production of the CC chemokine monocyte chemotactic protein-1", European Cytokine Network, vol. 10, No. 3, Sep. 1999, pp. 437-442.
Akira Endo, "The discovery and development of HMG-CoA reductase inhibitors", Journal of Lipid Research, vol. 33, (1992), pp. 1569-1582.
Jasper J. Haringman, et al., "Chemokine blockade: a new era in the treatment of rheumatoid arthritis?", Arthritis Res Ther, vol. 6, (2004), pp. 93-97.
Paul P. Tak, "Chemokine inhibition in inflammatory arthritis", Best Practice & Research Clinical Rheumatology, vol. 20, No. 5, (2006), pp. 929-939.
Takuji Iwamoto, et al., "Molecular aspects of rheumatoid arthritis: chemokines in the joints of patients", FEBS Journal, vol. 275, (2008), pp. 4448-4455.
Stephan Segerer, et al., "Chemokines, Chemokine Receptors, and Renal Disease: From Basic Science to Pathophysiologic and Therapeutic Studies", J. Am Soc Nephrol, vol. 11, (2000), pp. 152-176.
Elena Galkina, et al., "Leukocyte Recruitment and Vascular Injury in Diabetic Nephropathy", J. Am Soc Nephrol, vol. 17, (2006), pp. 368-377.
Takashi Wada, et al., "Chemokines in renal diseases", International Immunopharmacology, vol. 1, (2001), pp. 637-645.
R. John Baier, et al., "CC Chemokine Concentrations Increase in Respiratory Distress Syndrome and Correlate With Development of Bronchopulmonary Dysplasia", Pediatric Pulmonology, vol. 37, (2004), pp. 137-148.
Hiromi Shinoda, et al., "Elevated CC Chemokine Level in Bronchoalveolar Lavage Fluid Is Predictive of a Poor Outcome of Idiopathic Pulmonary Fibrosis", Respiration, vol. 78, (2009), pp. 285-292.
Willem I. de Boer, "Perspectives for cytokine antagonist therapy in COPD", Drug Discovery Today, vol. 10, No. 2, Jan. 2005, pp. 93-106.
Anna Sokolova, et al., "Monocyte Chemoattractant Protein-1 Plays a Dominant Role in the Chronic Inflammation Observed in Alzheimer's Disease", Brain Pathology, vol. 19, No. 3, (2009), pp. 392-398.
Paola Cinque, et al., "Elevated cerebrospinal fluid levels of monocyte chemotactic protein-1 correlate with HIV-1 encephalitis and local viral replication", AIDS, vol. 12, No. 11, (1998), pp. 1327-1332.
Don J. Mahad, et al., "The role of MCP-1 (CCL2) and CCR2 in multiple sclerosis and experimental autoimmune encephalomyelitis (EAE)", Seminars in Immunology, vol. 15, (2003), pp. 23-32.
Christian Vestergaard, et al., "Expression of CCR2 on Monocytes and Macrophages in Chronically Inflamed Skin in Atopic Dermatitis and Psoriasis", Acta Derm Venereol, vol. 84, (2004), pp. 353-358.
Bernhard Homey, et al, "Chemokines and other mediators as therapeutic targets in psoriasis vulgaris", Clinics in Dermatology, vol. 26, (2008), pp. 539-545.
Kensuke Egashira, "Molecular Mechanisms Mediating Inflammation in Vascular Disease: Special Reference to Monocyte Chemoattractant Protein-1", Hypertension, vol. 41, Part 2, (2003), pp. 834-841.
Ann Marie Schmidt, et al., "Chemokines on the Rise: MCP-1 and Restenosis", Arterioscler Thromb Vasc Biol., vol. 21, (2001), pp. 297-299.
Shiro Kitamoto, et al., "Stress and Vascular Responses: Antiinflammatory Therapeutic Strategy Against Atherosclerosis and Restenosis After Coronary Intervention", J. Pharmacol Sci, vol. 91, (2003), pp. 192-196.
James A. de Lemos, et al., "Serial Measurement of Monocyte Chemoattractant Protein-1 After Acute Coronary Syndromes", Journal of the American College of Cardiology, vol. 50, No. 22, (2007), pp. 2117-2124.

(56) References Cited

OTHER PUBLICATIONS

Ilaria Conti, et al., "CCL2 (monocyte chemoattractant protein-1) and cancer", Seminars in Cancer Biology, vol. 14, (2004), pp. 149-154.

Matt J. Craig, et al., "CCL2 (Monocyte Chemoattractant Protein-1) in cancer bone metastases", Cancer Metastasis Rev, vol. 25, (2006), pp. 611-619.

Hai Hu, et al., "Tumor Cell-Microenvironment Interaction Models Coupled with Clinical Validation Reveal CCL2 and Sncg as Two Predictors of Colorectal Cancer Hepatic Metastasis", Clin Cancer Res, vol. 15, No. 17, (2009), pp. 5485-5493.

Mingde Xia, et al., "Recent developments in CCR2 antagonists", Expert Opin. Ther. Patents, vol. 19, No. 3, (2009), pp. 295-303.

Hajime Kanda, et al., "MCP-1 contributes to macrophage infiltration into adipose tissue, insulin resistance, and hepatic steatosis in obesity", The Journal of Clinical Investigation, vol. 116, No. 6, Jun. 2006, pp. 1494-1505.

Stuart P. Weisberg, et al., "Obesity is associated with macrophage accumulation in adipose tissue", The Journal of Clinical Investigation, vol. 112, No. 12, Dec. 2003, pp. 1796-1808.

Peter Sartipy, et al., "Monocyte chemoattractant protein 1 in obesity and insulin resistance", PNAS, vol. 100, No. 12, Jun. 10, 2003, pp. 7265-7270.

Olga Stasikowska, et al., "Chemokines and chemokine receptors in glomerulonephritis and renal allograft rejection", Med Sci Monit, vol. 13, No. 2, (2007), pp. RA31-RA36.

Yasuo Sekine, et al., "Monocyte Chemoattractant Protein-1 and RANTES Are Chemotactic for Graft Infiltrating Lymphocytes during Acute Lung Allograft Rejection", American Journal of Respiratory Cell and Molecular Biology, vol. 23, (2000), pp. 719-726.

Lorenzo Piemonti, et al., "Human Pancreatic Islets Produce and Secrete MCP-1/CCL2: Relevance in Human Islet Transplantation", Diabetes, vol. 51, Jan. 2002, pp. 55-65.

U.S. Appl. No. 13/618,948, filed Sep. 14, 2012, Guglielmotti, et al.

\* cited by examiner

PHARMACEUTICAL COMPOSITION FOR THE TREATMENT OF MCP-1 MEDIATED INFLAMMATORY DISEASES

CROSS REFERENCES TO RELATED APPLICATIONS

This application is a 371 of International Patent Application No. PCT/EP10/062979, filed on Sep. 3, 2010, and claims priority to European Patent Application No. 09425368.9, filed on Sep. 23, 2009.

FIELD OF THE INVENTION

The present invention relates to a pharmaceutical composition for the treatment of MCP-1 mediated inflammatory diseases.

More in particular, the present invention relates to a pharmaceutical composition comprising a combination of 1-benzyl-3-hydroxymethylindazole, a pressure lowering agent selected from ACE-inhibitors, renin inhibitors, ARBs and CCBs, and/or a cholesterol lowering agent selected from statin derivatives. The combination showed an additive and synergistic activity in reducing MCP-1 levels, thus significantly improving inflammatory response inhibition and consequently reducing complications occurring in patients suffering from inflammatory diseases.

BACKGROUND OF THE ART

As it is known, MCP-1 (Monocyte Chemotactic Protein-1) is a protein belonging to the β subfamily of chemokines. MCP-1 has powerful chemotactic action on monocytes and exerts its action also on T lymphocytes, mastocytes and basophils (Rollins B. J., Chemokines, Blood 1997; 90: 909-928; M. Baggiolini, Chemokines and leukocyte traffic, Nature 1998; 392: 565-568).

Other chemokines belonging to the β subfamily are, for example, MCP-2 (Monocyte Chemotactic Protein-2), MCP-3, MCP-4, MIP-1α and MIP-1β, RANTES.

The β subfamily differs from the α subfamily in that, in the structure, the first two cysteines are adjacent for the β subfamily, whereas they are separated by an intervening amino acid for the α subfamily.

MCP-1 is produced by various types of cells (leukocytes, platelets, fibroblasts, endothelial cells and smooth muscle cells).

Among all the known chemokines, MCP-1 shows the highest specificity for monocytes and macrophages, for which it constitutes not only a chemotactic factor but also an activation stimulus, consequently inducing processes for producing numerous inflammatory factors (superoxides, arachidonic acid and derivatives, cytokines/chemokines) and amplifying the phagocytic activity.

The secretion of chemokines in general, and of MCP-1 in particular, is typically induced by various pro-inflammatory factors, for instance interleukin-1 (IL-1), interleukin-2 (IL-2), TNFα (Tumour Necrosis Factor Alpha), interferon-γ (interferon gamma) and bacterial lipopolysaccharide (LPS).

Prevention of the inflammatory response by blocking the chemokine/chemokine receptor system represents one of the main targets of pharmacological intervention (Gerard C. and Rollins B. J., Chemokines and disease. Nature Immunol. 2001; 2:108-115).

There is much evidence to suggest that MCP-1 plays a key role during inflammatory processes and has been indicated as a new and validated target in various pathologies.

Evidence of a considerable physiopathological contribution of MCP-1 has been obtained in the case of patients with articular and renal inflammatory diseases (rheumatoid arthritis, lupus nephritis, diabetic nephropathy and rejection following transplant).

However, more recently, MCP-1 has been indicated among the factors involved in inflammatory pathologies of the nervous system (multiple sclerosis, amyotrophic lateral sclerosis, Alzheimer's disease, HIV-associated dementia) and other pathologies and conditions, with and without an obvious inflammatory component, including atopic dermatitis, colitis, interstitial lung pathologies, restenosis, atherosclerosis, allograft rejection following a surgical intervention (for instance angioplasty, arterectomy, transplant, organ and/or tissue replacement, prosthesis implant), cancer (adenomas, carcinomas and metastases) and even metabolic diseases such as insulin resistance, diabetes and obesity.

In addition, despite the fact that the chemokine system is involved in controlling and overcoming viral infections, recent studies have demonstrated that the response of certain chemokines, and in particular of MCP-1, may have a harmful role in the case of host-pathogen interactions. In particular, MCP-1 has been indicated among the chemokines that contribute towards organ and tissue damage in pathologies mediated by alpha viruses characterized by monocyte/macrophage infiltration in the joints and muscles (Mahalingam S. et al. Chemokines and viruses: friend or foes? Trends in Microbiology 2003; 11: 383-391; Rulli N. et al. Ross River Virus: molecular and cellular aspects of disease pathogenesis. 2005; 107: 329-342).

European patent EP-B-0 382 276 describes a number of 1-benzyl-3-hydroxymethylindazole derivatives endowed with analgesic activity. In turn, European patent EP-B-0 510 748 describes, on the other hand, the use of these derivatives for preparing a pharmaceutical composition that is active in the treatment of autoimmune diseases. Finally, European patent EP-B-1 005 332 describes the use of these derivatives for preparing a pharmaceutical composition that is active in treating diseases derived from the production of MCP-1.

2-Methyl-2-[[1-(phenylmethyl)-1H-indazol-3-yl]methoxy]propanoic acid is thought to be capable of inhibiting, in a dose-dependent manner, the production of MCP-1 and TNF-a induced in vitro in monocytes from LPS and Candida albicans, whereas the same compound showed no effects in the production of cytokines IL-1 and IL-6, and of chemokines IL-8, MIP-1α, and RANTES (Sironi M. et al., "A small synthetic molecule capable of preferentially inhibiting the production of the CC chemokine monocyte chemotactic protein-1", European Cytokine Network. Vol. 10, No. 3, 437-41, September 1999).

Angiotensin II (A-II) is a potent vasoconstrictor that causes the muscles surrounding the blood vessels to contract, thereby significantly narrowing the blood vessels. This narrowing increases the pressure within arterial vessels, causing high blood pressure (hypertension).

Its generation in the renin-angiotensin cascade results from the action of an enzyme secreted by the kidneys, renin, on a blood plasma 2-globulin, angiotensinogen, to produce angiotensin I (A-I). A-I is then converted by angiotensin converting enzyme (ACE) to the octapeptide hormone, A-II.

In addition to renin-angiotensin system, calcium channels play an important role in pressure regulation. In both vascular and cardiac tissue, muscle cell contraction occurs when cells are depolarized from the influx of calcium through calcium channels in the cell. The increased cytosolic calcium binds to calmodulin, activating myosin light-chain kinase which phosphorylate myosin. The phosphorylated myosin can then interact with actin, resulting in muscle contraction. Calcium channel blockers inhibit muscle contraction and promote relaxation. In vascular smooth muscle this results in vessel dilation, reduced blood pressure (antihypertensive effect) and a reduction in the force required to pump blood by the heart.

Therefore, renin inhibitors, which inhibit the action of renin, ACE inhibitors, which inhibit the production of A-II, A-II receptor blockers or antagonists (ARBs), which inhibit the function of A-II, and calcium channel blockers or antagonists (CCBs) are useful in the treatment of hypertension.

The administration of ACE inhibitors, renin inhibitors, ARBs or CCBs results in the dilatation of the vessels and reduction of blood pressure, thereby making it easier for the heart to pump blood. ACE inhibitors, renin inhibitors, ARBs and CCbs can therefore also be used to improve heart failure as well as hypertension. In addition, they slow the progression of kidney disease due to high blood pressure or diabetes.

As a result of extensive studies, several patent and literature publications describe useful examples of ACE inhibitors, renin inhibitors, ARBs or CCBs for the treatment of heart failure and hypertension.

For example, WO2008/084504 describes several drugs in the class of ARBs, including candesartan (Atacand, AstraZeneca), eprosartan (Teveten, Solvay & Biovail), irbesartan (Avapro, BMS), losartan (Cozaar, Merck), olmesartan (Benicar, Medoxomil; Sankyo & Forest), telmisartan (Micardis, Boehringer Ingelheim), valsartan (Diovan, Novartis) and pratosartan (Kotobuki).

WO02/092081 describes several drugs in the class of ARBs, including candesartan cilexetil, eprosartan, irbesartan, losartan, tasosartan, telmisartan, and valsartan.

Renin inhibitors like aliskiren, ditekiren, enalkiren, remikiren, terlakiren, ciprokiren and zankiren are described in several patents and patent applications like U.S. Pat. No. 5,559,111, EP 173,481, EP 311,012, EP 416,373, EP 266, 950, EP 456,185, and EP 509,354.

US2008/0139511 describes several drugs in the class of ACE inhibitors, including benazepril, captopril, cilazapril, enalapril, enalaprilat, fosinopril, lisinopril, moexipril, perindopril, quinapril, ramipril, and trandolapril.

U.S. Pat. No. 5,977,159 describes the use of an ACE-inhibitor for treatment of dyspeptic symptoms, the ACE inhibitor being selected from alacepril, alatriopril, altiopril calcium, ancovenin, benazepril, benazepril hydrochloride, benazeprilat, benzazepril, benzoylcaptopril, captopril, captopril-cysteine, captopril-glutathione, ceranapril, ceranopril, ceronapril, cilazapril, cilazaprilat, converstatin, delapril, delapril-diacid, enalapril, enalaprilat, enalkiren, enapril, epicaptopril, foroxymithine, fosfenopril, fosenopril, fosenopril sodium, fosinopril, fosinopril sodium, fosinoprilat, fosinoprilic acid, glycopril, hemorphin-4, idapril, imidapril, indolapril, indolaprilat, libenzapril, lisinopril, lyciumin A, lyciumin B, mixanpril, moexipril, moexiprilat, moveltipril, muracein A, muracein B, muracein C, pentopril, perindopril, perindoprilat, pivalopril, pivopril, quinapril, quinapril hydrochloride, quinaprilat, ramipril, ramiprilat, spirapril, spirapril hydrochloride, spiraprilat, spiropril, spiropril hydrochloride, temocapril, temocapril hydrochloride, teprotide, trandolapril, trandolaprilat, utibapril, zabicipril, zabiciprilat, zofenopril and zofenoprilat.

Calcium channel blockers or antagonists (CCBs) are widely used alone or in combination with other antihypertensive drugs in the treatment of heart failure and hypertension. CCBs include dihydropyridine, phenylalkylamine, and benzothiazepine derivatives, and are widely described in patent and literature references, such as, for example, in U.S. Pat. Nos. 6,268,377 and 5,209,933, herein incorporated for reference.

The statins (or HMG-CoA reductase inhibitors) are a class of drugs that lower cholesterol levels in people with or at risk of cardiovascular disease. Statins lower cholesterol by inhibiting the enzyme HMG-CoA reductase, which is the rate-limiting enzyme of the mevalonate pathway of cholesterol synthesis. Inhibition of this enzyme in the liver results in decreased cholesterol synthesis as well as increased synthesis of LDL receptors, resulting in an increased clearance of low-density lipoprotein (LDL) from the bloodstream.

The statins are divided into two groups depending on their source. Fermentation-derived statins include lovastatin, mevastatin, pravastatin, simvastatin. Synthetic statins include atorvastatin, cerivastatin, fluvastatin, pitavastatin, and rosuvastatin.

The statins are described in a number of patent and literature publication, such as, for example, U.S. Pat. No. 6,911,472, U.S. Pat. No. 7,459,447, U.S. Pat. No. 7,498,359, U.S. Pat. No. 7,183,285, and Akira Endo, "The discovery and development of HMG-CoA reductase inhibitors" J. Lipid Res. Vol. 33 (1992), pp 1569-82.

SUMMARY OF THE INVENTION

Despite the activity developed so far, there is still the need for novel pharmaceutical compositions that are effective in the treatment of diseases based on the overexpression of MCP-1 or that are concurrently influenced by the overexpression of MCP-1.

The Applicant has surprisingly found that 1-benzyl-3-hydroxymethylindazole derivatives, in particular, 2-((1-benzyl-3-indazolyl)methoxy)-2-methylpropionic acid (also known as bindarit) administered in combination with a pressure lowering agent selected from ACE-inhibitors, renin inhibitors, ARBs and CCBs and/or a cholesterol lowering agent selected from statin derivatives can exert an additive and synergistic activity in reducing MCP-1 levels, thus significantly improve inflammatory response inhibition and consequently reducing complications occurring in patients suffering from inflammatory diseases.

In addition, since treatment of several inflammatory diseases is chronic in nature and possible undesirable and/or adverse effects could be experienced, doses of combined administration of 1-benzyl-3-hydroxymethylindazole derivatives, in particular, 2-((1-benzyl-3-indazolyl) methoxy)-2-methylpropionic acid (also known as bindarit), with a pressure lowering agent selected from ACE-inhibitors, ARBs, renin inhibitors and CCBs, and/or a cholesterol lowering agent selected from statin derivatives can be adjusted, for instance taking into account the type of pathology to be treated, the severity of the disease, the body weight of the patient, the dosage form, the chosen route of administration, the number of daily administrations and the efficacy of the chosen compound and agent(s), in order to improve tolerability without reducing the efficacy.

Accordingly, a first aspect of the present invention relates to a pharmaceutical composition comprising a 1-benzyl-3-hydroxymethylindazole derivative, at least one of (i) a pressure lowering agent selected from ACE-inhibitors, renin inhibitors, ARBs, and CCBs and/or (ii) a cholesterol lowering agent selected from statin derivatives, or any pharmaceutically acceptable salt and ester thereof, and at least one pharmaceutically acceptable vehicle.

In a second aspect, the present invention relates to the use of a composition comprising a 1-benzyl-3-hydroxymethylindazole derivative, at least one of (i) a pressure lowering agent selected from ACE-inhibitors, renin inhibitors, ARBs, and CCBs and/or (ii) a cholesterol lowering agent selected from statin derivatives, or any pharmaceutically acceptable salt and ester thereof, for preparing a pharmaceutical composition for the treatment or prevention of inflammatory diseases based on the expression of MCP-1.

As known in the art, inflammatory diseases based on the expression of MCP-1 particularly comprises articular diseases, renal diseases, cardiovascular diseases, pulmonary diseases, nervous system diseases, metabolic diseases, allograft rejection, and cancer. Advantageously, the present invention relates to the use of the above composition for the treatment or prevention of renal diseases and cardiovascular diseases.

In addition, in a further aspect, the present invention relates to a method for treating diseases based on the expression of MCP-1, particularly inflammatory diseases, and advantageously renal diseases and cardiovascular diseases, characterized by the administration to a person in need thereof an effective amount of a composition comprising a 1-benzyl-3-hydroxymethylindazole derivative, at least one of (i) a pressure lowering agent selected from ACE-inhibitors, renin inhibitors, ARBs and CCBs, and/or (ii) a cholesterol lowering agent selected from statin derivatives, or any pharmaceutically acceptable salt and ester thereof.

DETAILED DESCRIPTION OF THE INVENTION

Figure 1:
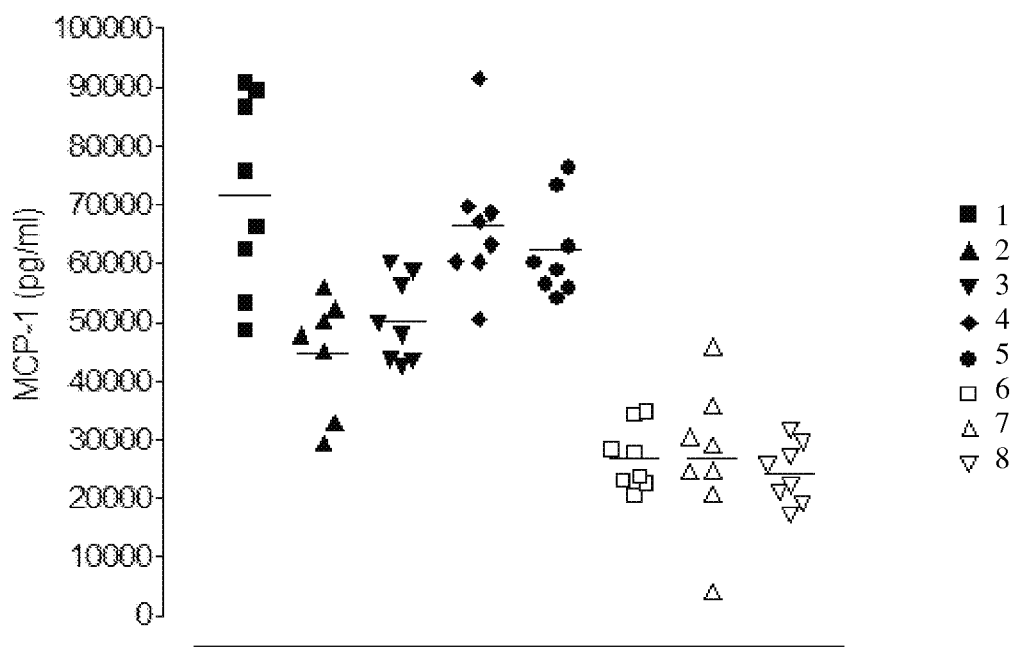
FIG. 1 is a Cartesian diagram illustrating the results of Example 1, described hereinbelow.

The 1-benzyl-3-hydroxymethylindazole derivative to be used in the composition of the present invention is represented by the following formula (I):

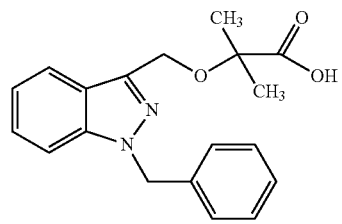

(I)

wherein $R_1$ and $R_2$, equal or different each other, are a hydrogen atom or a C1-C6 alkyl group, $R_3$, $R_4$, and $R_8$, equal or different each other, are a hydrogen atom or a C1-C5 alkyl group, a C1-C3 alkoxy group, or a halogen atom, $R_5$ is a hydrogen atom or a C1-C5 alkyl group, a C1-C3 alkoxy group, a halogen atom, or $R_5$ forms, together with one of $R_6$ and $R_7$, a cycle having five or six carbon atoms, $R_6$, and $R_7$ equal or different each other, are a hydrogen atom or a C1-C5 alkyl group, or one of $R_6$ and $R_7$ forms, together with $R_5$, a cycle having five or six carbon atoms, $R_{10}$ and $R_{11}$, equal or different each other, are a hydrogen atom or a C1-C5 alkyl group, and $R_{12}$ is a hydrogen atom or a C1-C4 alkyl group.

Preferably, $R_1$ and $R_2$, equal or different each other, are a hydrogen atom or a C1-C3 alkyl group.

Preferably, $R_3$, $R_4$, and $R_8$, equal or different each other, are a hydrogen atom, a methyl group, an ethyl group, a methoxy group, an ethoxy group, a chlorine atom, and a fluorine atom.

Advantageously, $R_5$ is a hydrogen atom, a methyl group, an ethyl group, a methoxy group, an ethoxy group, a chlorine atom, a fluorine atom, or $R_5$ forms, together with one of $R_6$ and $R_7$, a cycle having six carbon atoms, Preferably, $R_6$, and $R_7$ equal or different each other, are a hydrogen atom, a methyl group, an ethyl group, or one of $R_6$ and $R_7$ forms, together with $R_5$, a cycle having six carbon atoms, Advantageously, $R_{10}$ and $R_{11}$, equal or different each other, are a hydrogen atom or a C1-C3 alkyl group, and $R_{12}$ is a hydrogen atom or a C1-C3 alkyl group.

Particularly, the 1-benzyl-3-hydroxymethylindazole derivatives to be used in the composition of the present invention is the 2-((1-benzyl-3-indazolyl)methoxy)-2-methylpropionic acid (or bindarit) having the following structural formula.

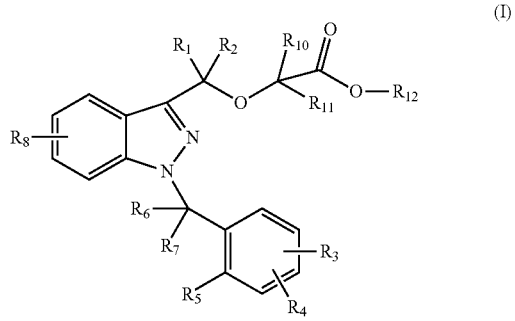

The pressure lowering agent selected from ACE-inhibitors to be used in the composition of the present invention is preferably selected from the group consisting of alacepril, alatriopril, altiopril calcium, ancovenin, benazepril, benazepril hydrochloride, benazeprilat, benzazepril, benzoylcaptopril, captopril, captopril-cysteine, captopril-glutathione, ceranapril, ceranopril, ceronapril, cilazapril, cilazaprilat, converstatin, delapril, delapril-diacid, enalapril, enalaprilat, enalkiren, enapril, epicaptopril, foroxymithine, fosfenopril, fosenopril, fosenopril sodium, fosinopril, fosinopril sodium, fosinoprilat, fosinoprilic acid, glycopril, hemorphin-4, idapril, imidapril, indolapril, indolaprilat, libenzapril, lisinopril, lyciumin A, lyciumin B, mixanpril, moexipril, moexiprilat, moveltipril, muracein A, muracein B, muracein C, pentopril, perindopril, perindoprilat, pivalopril, pivopril, quinapril, quinapril hydrochloride, quinaprilat, ramipril, ramiprilat, spirapril, spirapril hydrochloride, spiraprilat, spiropril, spiropril hydrochloride, temocapril, temocapril hydrochloride, teprotide, trandolapril, trandolaprilat, utibapril, zabicipril, zabiciprilat, zofenopril, zofenoprilat, pharmaceutically acceptable salts thereof, and mixture thereof.

Advantageously, the pressure lowering agent selected from ACE-inhibitors to be used in the composition of the present invention is selected from the group consisting of captopril, enalapril, lisinopril, ramipril, and perindopril.

Preferably, the pressure lowering agent selected from ACE-inhibitors to be used in the composition of the present invention is represented by the following formula (II):

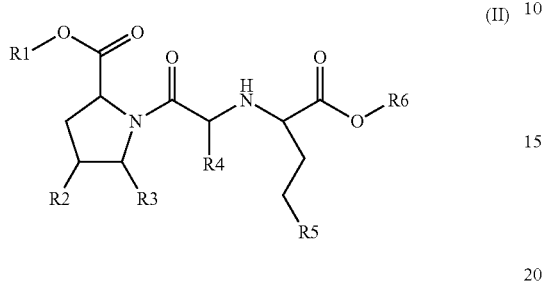

(II)

wherein
R1 is a hydrogen atom, or R1 forms a pharmaceutically acceptable basic addition salt;
R2 and R3, equal or different each other, are, independently, a hydrogen atom; or R2 and R3 together form an aromatic or aliphatic cycle having five or six carbon atoms;
R4 is a C1-C4 alkyl group or a C1-C4 alkylamino group;
R5 is a methyl or phenyl group;
R6 is a hydrogen atom, or a methyl or ethyl group.

Particularly, the pressure lowering agent selected from ACE-inhibitors to be used in the composition of the present invention is ramipril.

The pressure lowering agent selected from ARBs to be used in the composition of the present invention is preferably selected from the group consisting of candesartan, cilexetil, eprosartan, irbesartan, losartan, olmesartan, tasosartan, telmisartan, valsartan, and pratosartan.

Advantageously, the pressure lowering agent selected from ARBs to be used in the composition of the present invention is selected from the group consisting of candesartan, irbesartan, losartan, and valsartan.

Preferably, the pressure lowering agent selected from ARBs to be used in the composition of the present invention is represented by the following formula (III):

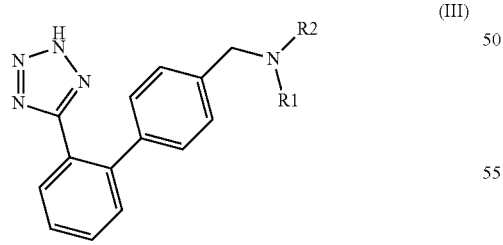

(III)

wherein
R1 and R2 equal or different each other, are, independently, a C1-C5 alkyl group, optionally substituted with an oxo group or a carboxyl group; or R1 and R2 together form an aromatic or aliphatic heterocycle, comprising 1 or 2 N atoms and optionally substituted.

Advantageously, said aromatic heterocycle has one of the following formulas:

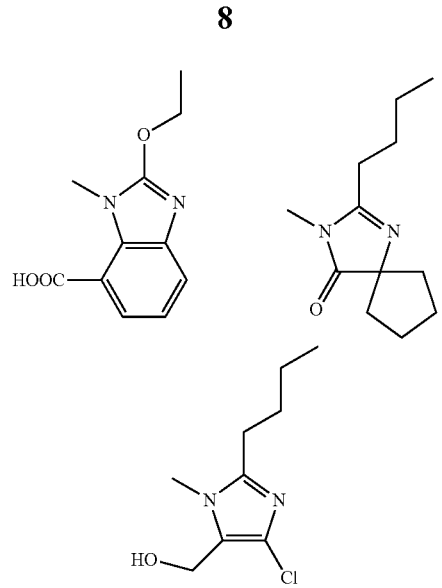

Particularly, the pressure lowering agent selected from ARBs to be used in the composition of the present invention is losartan or irbesartan.

The pressure lowering agent selected from renin inhibitors to be used in the composition of the present invention is preferably selected from the group consisting of aliskiren, ditekiren, enalkiren, remikiren, terlakiren, ciprokiren and zankiren.

Advantageously, the pressure lowering agent selected from renin inhibitors to be used in the composition of the present invention is selected from the group consisting of aliskiren and remikiren.

In particular, aliskiren has the following formula:

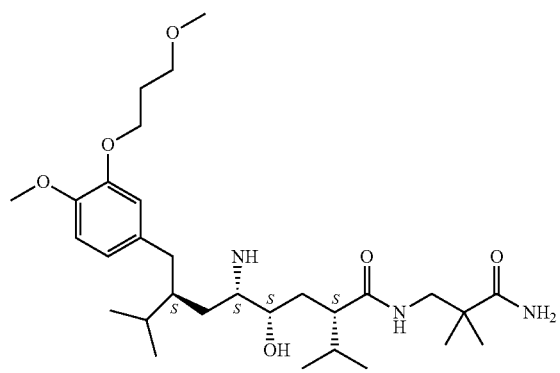

and remikiren has the following formula:

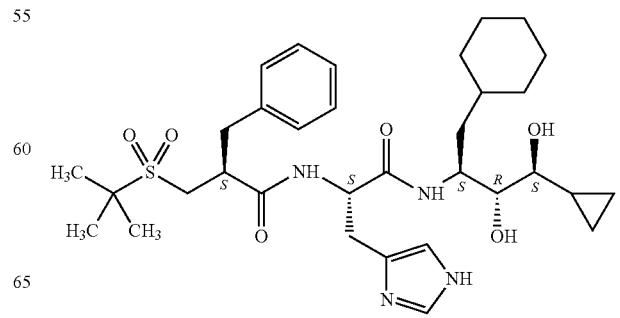

Particularly, the pressure lowering agent selected from renin inhibitors to be used in the composition of the present invention is aliskiren.

The pressure lowering agent selected from CCBs to be used in the composition of the present invention is preferably selected from the group consisting of amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, diltiazem, clentiazem, bepridil, bencyclane, etafenone, flunarizine, lidoflazine, lomerizine, mibefradil, phendilin, prenylamine, semotiadil, terodiline, gallopamil, and verapamil.

More preferably, the CCBs to be used in the composition of the present invention is selected from the group consisting of amlodipine, bamidipine, felodipine, isradipine, lacidipine, lercanidipine, manidipine, nicardipine, nifedipine, nimodipine, nisoldipine, nitrendipine, diltiazem, gallopamil, and verapamil.

Advantageously, the CCBs to be used in the composition of the present invention is selected from the group consisting of amlodipine, lacidipine, nifedipine, verapamil, and diltiazem.

Particularly, the CCBs to be used in the composition of the present invention is selected from the group consisting of amlodipine, verapamil, and diltiazem.

More in particular, amlodipine has the following formula:

verapamil has the following formula:

and diltiazem has the following formula:

The cholesterol lowering agent selected from statin derivatives to be used in the composition of the present invention is preferably selected from the group consisting of atorvastatin, cerivastatin, fluvastatin, lovastatin, mevastatin, pitavastatin, pravastatin, rosuvastatin, and simvastatin.

Advantageously, the cholesterol lowering agent selected from statin derivatives to be used in the composition of the present invention is selected from the group consisting of atorvastatin, fluvastatin, lovastatin, pravastatin, rosuvastatin and simvastatin.

Preferably, the cholesterol lowering agent selected from statin derivatives to be used in the composition of the present invention is represented by the following formula (IV):

(IV)

wherein
A is a —$CH_2CH_2$— group or a —CH=CH— group;
W, X, Y, and K, equal or different each other, are independently a C or N atom;
n is 0 or 1;
R1 is a hydrogen atom or a N-phenyl-formamide group when Y is a C atom;
R2 is a hydrogen atom; a phenyl group; a N-alkyl-alkylsulfonamide group, wherein the alkyl groups contain, independently, from 1 to 3 C atoms;
or
R1 and R2, when Y is a C atom, together form an aromatic or aliphatic cycle having five or six carbon atoms.

Preferably, the cholesterol lowering agent selected from statin derivatives to be used in the composition of the present invention is represented by the following formula (V):

(V)

wherein
R1 is a methyl group or a hydroxyl group;
R2 is a C1-C5 linear or branched alkyl group;
R3 is a hydroxyl group;
R4 is a carboxyl group;
or
R3 and R4, together, form a δ-lactone group.

Particularly, the cholesterol lowering agent selected from statin derivatives to be used in the composition of the present invention is simvastatin or atorvastatin.

In particular, the inflammatory pathologies associated with the expression of MCP-1 are articular diseases, like rheumatoid arthritis, arthritis induced by viral infections, psoriatic arthritis, arthrosis (Haring-man J J and Tak P P, *Chemokine blockade: a new era in the treatment of rheumatoid arthritis?*, Arthritis Res Ther 2004; 6:93-97; Tak P P, *Chemokine inhibition in inflammatory arthritis. Best Practice & Research Clinical Rheumatology*, 2006; 20:929-939; Iwamoto T et al., *Molecular aspects of rheumatoid arthritis: chemokines in the joints of patients*, FEBS Journal 2008; 275:4448-4455; Mahalingam S. et al., *Chemokines and viruses: friend or foes? Trends in Microbiology*, 2003; 11: 383-391; Rulli N. et al., *Ross River Virus: molecular and cellular aspects of disease pathogenesis*, 2005; 107: 329-342), renal diseases, like lupus nephritis, diabetic nephropathy, glomerulonephritis, polycystic kidney disease (Segerer S et al., Chemokines, *Chemokine Receptors, and Renal Disease From Basic Science To Pathophysiologic and Therapeutic Studies*, J Am Soc Nephrol 2000; 11:152-176; Galkina E and Ley K., *Leukocyte Recruitment and Vascular Injury in Diabetic Nephropathy*, J Am Soc Nephrol 2006; 17:368-377; Wada T et al., *Chemokines in renal diseases. International Immunopharmacology*, 2001; 1:637-645) pulmonary diseases, like interstitial lung disease, fibrosis (Baier R J et al., *CC Chemokine Concentrations Increase in Respiratory Distress Syndrome and Correlate With Development of Bronchopulmonary Dysplasia*, Pediatric Pulmonology 2004; 37:137-148; Shinoda H et al., *Elevated CC Chemokine Level in Bronchoalveolar Lavage Fluid Is Predictive of a Poor Outcome of Idiopathic Pulmonary Fibrosis*, Respiration 2008; de Boer W I., *Perspectives for cytokine antagonist therapy in COPD*, Drug Discovery Today 2005; 10(2):93-106), nervous system diseases, like multiple sclerosis, Alzheimer's disease, HIV-associated dementia (Sokolova A et al., *Monocyte Chemoattractant Protein-1 Plays a Dominant Role in the Chronic Inflammation Observed in Alzheimer's Disease*, Brain Pathology 2009; 19(3):392-8; Cinque P et al., *Elevated cerebrospinal fluid levels of monocyte chemotactic protein-1 correlate with HIV-1 encephalitis and local viral replication*, AIDS 1998; 12:1327-1332; Mahad D J and Ransohoff R M, *The role of MCP-1 (CCL2) and CCR2 in multiple sclerosis and experimental autoimmune encephalomyelitis (EAE)*, Seminars in Immunology. 2003; 15:23-32), atopic dermatitis, psoriasis (Vestergaard C et al., *Expression of CCR2 on Monocytes and Macrophages in Chronically Inflamed Skin in Atopic Dermatitis and Psoriasis*, Acta Derm Venereol 2004; 84:353-358; Homey B and Meller S., *Chemokines and other mediators as therapeutic targets in psoriasis vulgaris*, Clinics in Dermatology 2008; 26:539-545), cardiovascular diseases, like vasculitis, restenosis, atherosclerosis, myocardial infarction, angina, acute coronary diseases (Egashira K., *Molecular Mechanisms Mediating Inflammation in Vascular Disease: Special Reference to Monocyte Chemoattractant Protein-1*, Hypertension. 2003; 41 [part 2]:834-841; Schmidt A M and Stern D M, *Chemokines on the Rise: MCP-1 and Restenosis*, Arterioscler Thromb Vasc Biol. 2001; 21:297-299; Kitamoto S et al., *Stress and Vascular Responses: Anti-inflammatory Therapeutic Strategy Against Atherosclerosis and Restenosis After Coronary Intervention*, J Pharmacol Sci 2003; 91:192-196; de Lemos J A et al., *Serial Measurement of Monocyte Chemoattractant Protein-1 After Acute Coronary Syndromes*, J Am Coll Cardiol. 2007; Vol. 50, No. 22: 2117-2124), cancers, like adenomas, carcinomas and metastases (Conti C and Rollins B J, *CCL2 (monocyte chemoattractant protein-1) and cancer*, Seminars in Cancer Biology 2004; 14:149-154; Craig M J and Loberg R D, *CCL2 (Monocyte Chemoattractant Protein-1) in cancer bone metastases*, Cancer Metastasis Rev 2006; 25:611-619; Hu H et al., *Tumor Cell-Microenvironment Interaction Models Coupled with Clinical Validation Reveal CCL2 and SNCG as Two Predictors of Colorectal Cancer Hepatic Metastasis*, Clin Cancer Res 2009; 15(17):5485-93), metabolic diseases, like insulin resistance, type II diabetes and obesity (Xia M and Sui Z, *Recent development in CCR2 antagonists*, Expert Opin Ther Patents 2009; 19(3):295-303; Kanda H et al., *MCP-1 contributes to macrophage infiltration into adipose tissue, insulin resistance, and hepatic steatosis in obesity*, J. Clin. Invest. 116:1494-1505; Weisberg S P et al., *Obesity is associated with macrophage accumulation in adipose tissue*, J. Clin. Invest. 2003; 112: 1796-1808; Sartipy P and Loskutoff D J, *Monocyte chemoattractant protein 1 in obesity and insulin resistance*, PNAS 2003; 100(12): 7265-7270) and allograft rejection following surgical interventions such as, for example, angioplasty, arterectomy, circulation recovery techniques, transplants, organ replacements, tissue replacements and prosthesis implants (Stasikowska O, *Chemokines and chemokine receptors in glomerulonephritis and renal allograft rejection*, Med Sci Monit, 2007; 13(2): RA31-36; Sekine Y et al., *Monocyte Chemoattractant Protein-1 and RANTES Are Chemotactic for Graft Infiltrating Lymphocytes during Acute Lung Allograft Rejection*, Am. J. Respir. Cell Mol. Biol. 2000; Vol. 23, pp. 719-726; Piemonti L et al., *Human Pancreatic Islets Produce and Secrete MCP-1/CCL2: Relevance in Human Islet Transplantation*, Diabetes 2002; 51:55-65).

Preferably, the pharmaceutical composition of the present invention is prepared in suitable dosage forms comprising an effective dose of:
  at least one compound of formula (I), or a pharmaceutically acceptable salt and ester thereof,
  at least one of (i) a pressure lowering agent selected from ACE-inhibitors, renin inhibitors, ARBs, and CCBs or a pharmaceutically acceptable salt and ester thereof, or (ii) a cholesterol lowering agent selected from statin derivatives or a pharmaceutically acceptable salt and ester thereof, and
  at least one pharmaceutically acceptable vehicle.

Depending on the nature of the substituents, the compound of formula (I), the pressure lowering agent, and the cholesterol lowering agent may form addition salts with physiologically acceptable organic or mineral acids or bases.

Typical examples of suitable physiologically acceptable mineral acids are hydrochloric acid, hydrobromic acid, sulfuric acid, phosphoric acid and nitric acid.

Typical examples of suitable physiologically acceptable organic acids are acetic acid, ascorbic acid, benzoic acid, citric acid, fumaric acid, lactic acid, maleic acid, methanesulfonic acid, oxalic acid, paratoluenesulfonic acid, benzenesulfonic acid, succinic acid, tannic acid and tartaric acid.

Typical examples of suitable physiologically acceptable mineral bases are hydroxides, carbonates and hydrogen carbonates of ammonium, calcium, magnesium, sodium and potassium, for instance ammonium hydroxide, calcium hydroxide, magnesium carbonate, sodium hydrogen carbonate and potassium hydrogen carbonate.

Typical examples of suitable physiologically acceptable organic bases are: arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, N-methylglucamine, glucamine, glucosamine, histidine, N-(2-hydroxyethyl)piperidine, N-(2-hydroxyethyl)pyrrolidine, isopropylamine, lysine, methylglucamine, morpholine, piperazine, piperidine, theobromine, triethylamine, trimethylamine, tripropylamine and tromethamine.

Depending on the nature of the substituents, the compound of formula (I), the pressure lowering agent, and the cholesterol lowering agent may form esters with physiologically acceptable organic acids.

Typical examples of suitable physiologically acceptable organic acids are acetic acid, ascorbic acid, benzoic acid, citric acid, fumaric acid, lactic acid, maleic acid, methanesulfonic acid, oxalic acid, paratoluenesulfonic acid, benzenesulfonic acid, succinic acid, tannic acid and tartaric acid.

The composition of the present invention also include the stereoisomers and enantiomers of the compound of formula (I), the pressure lowering agent, and the cholesterol lowering agent described above.

The terms "pharmaceutically acceptable" and "physiologically acceptable" are intended to define, without any particular limitation, any material suitable for preparing a pharmaceutical composition to be administered to a living being.

Examples of pharmaceutically acceptable vehicles known in the prior art are, for example, glidants, binders, disintegrants, fillers, diluents, flavourings, colorants, fluidizers, lubricants, preserving agents, humectants, absorbents and sweeteners.

Useful examples of pharmaceutically acceptable vehicles are sugars, such as lactose, glucose or sucrose, starches, such as corn starch and potato starch, cellulose and derivatives thereof, for instance sodium carboxymethylcellulose, ethylcellulose and cellulose acetate, gum tragacanth, malt, gelatin, talc, cocoa butter, waxes, oils, such as groundnut oil, cottonseed oil, safflower oil, sesame oil, olive oil, corn oil and soybean oil, glycols such as propylene glycol, polyols such as glycerol, sorbitol, mannitol and polyethylene glycol, esters such as ethyl oleate and ethyl laurate, agar-agar, and the like.

Examples of suitable dosage forms are tablets, capsules, coated tablets, granules, solutions and syrups for oral administration; medicated plasters, solutions, pastes, creams and ointments for transdermal administration; suppositories for rectal administration and sterile solutions for injection or aerosol administration.

Other suitable dosage forms are sustained-release forms and liposome-based forms, for either the oral or injection route.

The dosage forms may also contain other conventional ingredients such as: preserving agents, stabilizers, surfactants, buffers, osmotic pressure regulators, emulsifiers, sweeteners, colorants, flavourings and the like.

When required for particular therapies, the pharmaceutical composition of the present invention may contain other pharmacologically active ingredients whose simultaneous administration is useful.

The amount of the compound of formula (I), the pressure lowering agent selected from ACE-inhibitors, renin inhibitors, ARBs, and CCBs and/or (ii) the cholesterol lowering agent selected from statins, or of pharmaceutically acceptable salt and ester thereof, in the pharmaceutical composition of the present invention may vary within a wide range as a function of known factors, for instance the type of pathology to be treated, the severity of the disease, the body weight of the patient, the dosage form, the chosen route of administration, the number of daily administrations and the efficacy of the chosen compound and agent(s).

However, the optimum amount may be determined simply and routinely by a person skilled in the art.

Typically, the amount of the compound of formula (I) or of pharmaceutically acceptable salt and ester thereof in the pharmaceutical composition of the present invention will be such that it ensures a level of administration of between 0.1 and 100 mg/kg/day. Preferably, the level of administration is between 1 and 50 mg/kg/day and even more preferably between 2 and 35 mg/kg/day.

More particularly, the pharmaceutical composition of the present invention comprises an amount of bindarit able to ensure a level of administration of between 10 and 20 mg/kg/day.

Typically, the amount of the pressure lowering agent selected from ACE-inhibitors, or a pharmaceutically acceptable salt and ester thereof, in the pharmaceutical composition of the present invention will be such that it ensures a level of administration of between 0.005 and 2.5 mg/kg/day, preferably between 0.01 and 1 mg/kg/day.

More particularly, the pharmaceutical composition of the present invention comprises an amount of ramipril able to ensure a level of administration of between 0.04 and 0.08 mg/kg/day.

Typically, the amount of the pressure lowering agent selected from ARBs, or a pharmaceutically acceptable salt and ester thereof, in the pharmaceutical composition of the present invention will be such that it ensures a level of administration of between 0.05 and 15 mg/kg/day, preferably between 0.2 and 10 mg/kg/day.

More particularly, the pharmaceutical composition of the present invention comprises an amount of losartan able to ensure a level of administration of between 0.2 and 2 mg/kg/day or an amount of irbesartan able to ensure a level of administration of between 1.0 and 10 mg/kg/day.

Typically, the amount of the pressure lowering agent selected from renin inhibitors, or a pharmaceutically acceptable salt and ester thereof, in the pharmaceutical composition of the present invention will be such that it ensures a level of administration of between 1.0 and 20 mg/kg/day, preferably between 2.5 and 10 mg/kg/day.

More particularly, the pharmaceutical composition of the present invention comprises an amount of aliskiren able to ensure a level of administration of between 2.5 and 5 mg/kg/day.

Typically, the amount of the pressure lowering agent selected from CCBs, or a pharmaceutically acceptable salt and ester thereof, in the pharmaceutical composition of the present invention will be such that it ensures a level of administration of between 0.05 and 15 mg/kg/day, preferably between 0.08 and 10 mg/kg/day.

More particularly, the pharmaceutical composition of the present invention comprises an amount of amlodipine able to ensure a level of administration of between 0.08 and 0.17 mg/kg/day or an amount of verapamil able to ensure a level of administration of between 3.00 and 6.00 mg/kg/day or an amount of diltiazem able to ensure a level of administration of between 2.00 and 8.00 mg/kg/day.

Typically, the amount of the cholesterol lowering agent selected from statin derivatives, or of pharmaceutically acceptable salt and ester thereof in the pharmaceutical composition of the present invention will be such that it ensures a level of administration of between 0.03 and 2.0 mg/kg/day, preferably between 0.1 and 1.0 mg/kg/day.

More particularly, the pharmaceutical composition of the present invention comprises an amount of simvastatin able to ensure a level of administration of between 0.1 and 1 mg/kg/day or an amount of atorvastatin able to ensure a level of administration of between 0.1 and 1 mg/kg/day.

The dosage forms of the pharmaceutical composition of the present invention may be prepared according to techniques that are well known to pharmaceutical chemists, including mixing, granulation, compression, dissolution, sterilization and the like.

In particular, the preferred dosage form is a tablet for oral administration. More particularly, the tablet for oral administration comprises a combination of a compound of formula (I), preferably bindarit, with at least one pressure or cholesterol lowering agent selected from the group consisting of ramipril, losartan, irbesartan, aliskiren, amlodipine, verapanil, diltiazem, simvastatin, and atorvastatin.

Even more particularly, the pharmaceutical composition according to the present invention, preferably a tablet for oral administration, comprises from 300 to 1200 mg of bindarit, and an amount of at least one pressure or cholesterol lowering agent selected from the group consisting of ramipril, losartan, irbesartan, aliskiren, amlodipine, verapanil, diltiazem, simvastatin, and atorvastatin showed in the following table A. Table A also shows the useful and preferred range of weight ratio between the amount of bindarit and the amount of the pressure or cholesterol lowering agent under consideration in the pharmaceutical composition according to the present invention.

TABLE A

| | Minimum amount mg | Maximum amount mg | Weight Ratio Useful Range | Weight Ratio Preferred Range |
|---|---|---|---|---|
| ramipril | 2.5 | 10 | 30-480 | 100-150 |
| losartan | 25 | 100 | 3-48 | 10-15 |
| irbesartan | 75 | 300 | 1-16 | 2-8 |
| aliskiren | 150 | 300 | 1-8 | 2-4 |
| amlodipine | 5 | 10 | 30-240 | 60-120 |
| verapanil | 120 | 480 | 0.5-10 | 1-5 |
| diltiazem | 180 | 360 | 1.5-10 | 3-5 |
| simvastatin | 10 | 40 | 7.5-120 | 10-50 |
| atorvastatin | 10 | 40 | 7.5-120 | 10-50 |

The examples that follow are intended to illustrate the present invention without, however, limiting it in any way.

Example 1

Effect on MCP-1 Plasma Levels in Mice

The capacity of the compound to inhibit MCP-1 circulating levels induced by LPS (lipopolysaccharide) in mice has been tested giving bindarit alone or in combination with ramipril or losartan, as prototypes of antihypertensive drugs, or simvastatin, as prototype of cholesterol lowering drugs. Ramipril is an ACE (angiotensin converting enzyme) inhibitor and losartan is an angiotensin receptor blockers (ARBs).

MCP-1 plasma levels were measured by commercially available ELISA kit.

Drugs were intraperitoneally (ip) administered 30 minutes before LPS injection (50 μg/mouse, ip) to groups of eight mice. At 3 hours following LPS injection, mice were anesthetized and blood was withdrawn by intracardiac puncture in order to obtain plasma (heparinized samples) to be used to measure MCP-1 levels.

The results are summarized in the following Table 1 as average of eight measurements and in FIG. 1. The percent reduction was calculated versus the vehicle group.

TABLE 1

| | Drug administration group | MCP-1 plasma level (μg/ml) | % reduction |
|---|---|---|---|
| 1 | Vehicle | 71.6 | — |
| 2 | Bindarit 200 mg/kg | 44.8* | 45 |
| 3 | Ramipril 5 mg/kg | 50.3* | 30 |
| 4 | Losartan 1 mg/kg | 62.2 | 13 |
| 5 | Simvastatin 1 mg/kg | 66.4 | 7 |
| 6 | Bindarit 200 mg + Ramipril 5 mg/kg | 26.8*# | 63 |
| 7 | Bindarit 200 mg + Losartan 1 mg/kg | 26.9*# | 62 |
| 8 | Bindarit 200 mg + Simvastatin 1 mg/kg | 24.2*# | 66 |

*$p < 0.01$ versus vehicle group,
$p < 0.01$ versus each drug administered alone The data of Table 1 and FIG. 1 clearly demonstrated that the combination of bindarit with ramipril or simvastatin or losartan showed an additive and synergistic effect compared to the activity of each single drug given alone, resulting in over 60% reduction of MCP-1 plasma level.

Example 2

Effect on Proteinuria in Human

A total of 80 male and female patients from 30 to 70 years old suffering from Type 2 diabetes have been treated. 40 patients received bindarit (600 mg) twice a day and irbesartan (300 mg) once a day, 40 patients received placebo twice a day and irbesartan (300 mg) once a day. Irbesartan is a well known angiotensin receptor blockers (ARB). The treatment lasted 8 weeks.

Before beginning treatment and at the end thereof UAE (Urinary Albumin Excretion) has been measured by nephelometric method.

The results are reported in the following Table 2 and in FIG. 2.

The activity has been reported as percentage of patients with a UAE reduction equal to or higher than 25% with respect to basal value (UAE level before beginning treatment).

TABLE 2

| | Drug administration group | Patient percentage |
|---|---|---|
| A | Bindarit 600 mg + Irbesartan 300 mg | 47.6% |
| B | Placebo + Irbesartan 300 mg | 27.5% |

Figure 2:
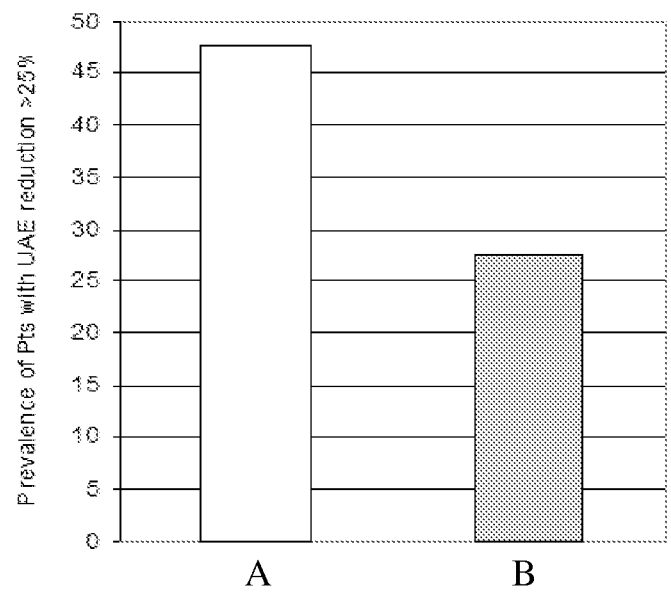
FIG. 2 is a Cartesian diagram illustrating the results of Example 2, described hereinbelow.

The data of Table 2 and FIG. 2 clearly demonstrated that at the end of the study the percentage of patients with a UAE reduction equal to or higher than 25% with respect to the basal value resulted significantly higher in the group receiving the combination bindarit and irbesartan compared to the group receiving the combination placebo and irbesartan.

Example 3

Effect on MCP-1 Plasma Levels in Mice

The capacity of the compound to inhibit MCP-1 circulating levels induced by LPS (lipopolysaccharide) in mice has been tested giving bindarit alone or in combination with verapamil or nifedipine, as prototypes of Cα antagonist antihypertensive drugs.

MCP-1 plasma levels were measured by commercially available ELISA kit.

Drugs were intraperitoneally (ip) administered 30 minutes before LPS injection (50 µg/mouse, ip) to groups of six mice. At 3 hours following LPS injection, mice were anesthetized and blood was withdrawn by intracardiac puncture in order to obtain plasma (heparinized samples) to be used to measure MCP-1 levels.

The results are summarized in the following Table 3 as average of six measurements and in FIG. 3. The percent reduction was calculated versus the vehicle group.

TABLE 3

| | Drug administration group | MCP-1 plasma level (µg/ml) | % reduction |
|---|---|---|---|
| 1 | Vehicle | 59.7 | — |
| 2 | Bindarit 200 mg/kg | 35.8** | 40 |
| 3 | Verapamil 10 mg/kg | 44.3 | 26 |
| 4 | Nifedipine 10 mg/kg | 32.2** | 45 |
| 5 | Bindarit 200 mg + Verapamil 10 mg/kg | 15.2**# | 74 |
| 6 | Bindarit 200 mg + Nifedipine 10 mg/kg | 9.8**§ | 84 |

Figure 3:
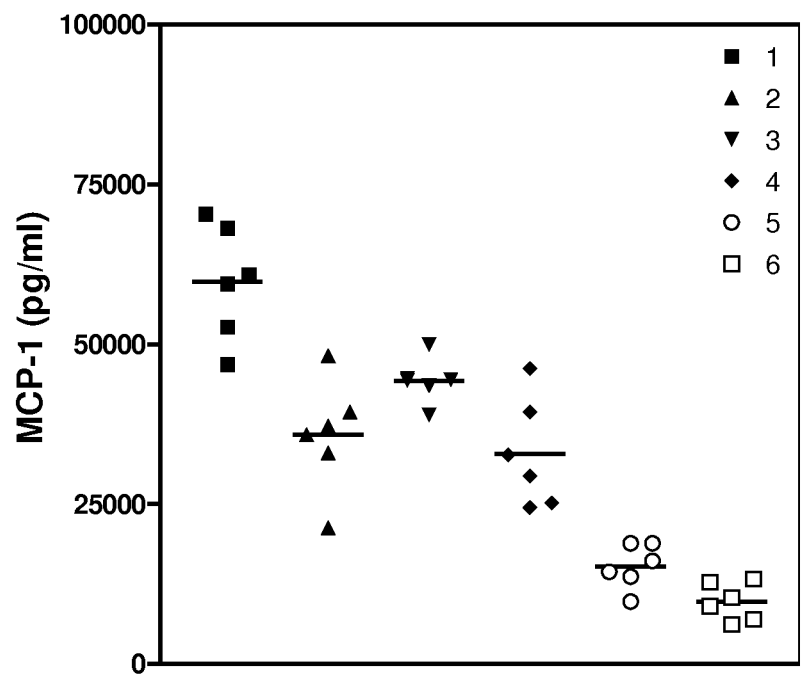
FIG. 3 is a Cartesian diagram illustrating the results of Example 3, described hereinbelow.

**$p < 0.01$ vs vehicle group
$p < 0.05$ vs bindarit and verapamil given alone
§$p < 0.01$ vs bindarit and nifedipine given alone The data of Table 3 and FIG. 3 clearly demonstrated that the combination of bindarit with verapamil or nifedipine showed an additive and synergistic effect compared to the activity of each single drug given alone, resulting in over 74% and 84% reduction of MCP-1 plasma level, respectively.

The invention claimed is:

1. A pharmaceutical composition, comprising:
    (a) bindarit; and
    (b) irbesartan,
    wherein said (a) bindarit and said (b) irbesartan are present in a weight ratio of 2:1 to 200:1.
2. A pharmaceutical composition according to claim 1, further comprising:
    (c) at least one pharmaceutically acceptable vehicle.
3. A pharmaceutical composition according to claim 1, wherein said (a) bindarit and said (b) irbesartan are present in a weight ratio of 2:1 to 100:1.
4. A pharmaceutical composition according to claim 3, further comprising:
    (c) at least one pharmaceutically acceptable vehicle.
5. A pharmaceutical composition according to claim 1, wherein said (a) bindarit and said (b) irbesartan are present in a weight ratio of 2:1 to 16:1.
6. A pharmaceutical composition according to claim 5, further comprising:
    (c) at least one pharmaceutically acceptable vehicle.
7. A pharmaceutical composition according to claim 5, wherein said (a) bindarit and said (b) irbesartan are present in a weight ratio of 2:1 to 8:1.
8. A pharmaceutical composition according to claim 7, further comprising:
    (c) at least one pharmaceutically acceptable vehicle.
9. A dosage unit, comprising:
    (a) 600 mg of bindarit; and
    (b) 300 mg of irbesartan.
10. A dosage unit according to claim 9, further comprising:
    (c) at least one pharmaceutically acceptable vehicle.

* * * * *